United States Patent [19]

Innemee et al.

[11] 4,400,378
[45] Aug. 23, 1983

[54] PHARMACEUTICAL COMPOSITION FOR THE TREATMENT OF GLAUCOMA

[75] Inventors: Hendricus C. Innemee; Jacobus C. A. van Meel, both of Amsterdam; Adriaan De Jonge, Driebergen; Petrus B. M. W. M. Timmermans, Ouderkerk a.d. Amstel; Pieter A. van Zwieten, Amsterdam, all of Netherlands

[73] Assignee: Karl Thomae Gesellschaft mit beschränkter Haftung, Biberach an der Riss, Fed. Rep. of Germany

[21] Appl. No.: 317,260

[22] Filed: Nov. 2, 1981

[51] Int. Cl.³ ............................................. A61K 31/33
[52] U.S. Cl. .................................................. 424/244
[58] Field of Search ............................... 424/270, 244

[56] References Cited

U.S. PATENT DOCUMENTS 3,804,849  4/1974  Griss et al. ........................... 424/270

Primary Examiner—Douglas W. Robinson

Attorney, Agent, or Firm—Hammond & Littell, Weissenberger & Muserlian

[57] ABSTRACT

The method of treating glaucoma with compounds of the formula

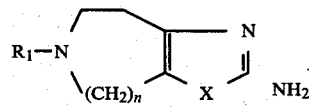

wherein
$R_1$ is hydrogen, alkyl of 1 to 4 carbon atoms, hydroxy-(alkyl of 1 to 4 carbon atoms), benzyl, halobenzyl, methyl-benzyl, methoxy-benzyl or allyl;
X is oxygen or sulfur; and
n is 2 or, when X is sulfur, also 1;
or non-toxic, pharmacologically acceptable acid addition salts thereof, and pharmaceutical compositions for use in said treatment.

7 Claims, No Drawings

PHARMACEUTICAL COMPOSITION FOR THE TREATMENT OF GLAUCOMA

This invention relates to novel pharmaceutical compositions for the treatment of glaucoma, as well as to a method of treating glaucoma with certain derivatives of thiazole or oxazole.

THE PRIOR ART

Belgian Pat. Nos. 684,415 and 771,330 and U.S. Pat. No. 3,804,849 disclose, inter alia, certain thiazolo and oxazolo compounds of the formula

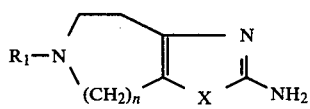

wherein
$R_1$ is hydrogen, alkyl of 1 to 4 carbon atoms, hydroxy-(alkyl of 1 to 4 carbon atoms), benzyl, halobenzyl, methyl-benzyl, methoxy-benzyl or allyl;
X is oxygen or sulfur; and
n is 2 or, when X is sulfur, also 1;
and non-toxic, pharmacologically acceptable acid addition salts thereof.

Specific examples of substituent $R_1$ are hydrogen, methyl, ethyl, propyl, isopropyl, butyl, isobutyl, tert.butyl, 2-hydroxy-ethyl, 2-hydroxy-propyl, 3-hydroxy-propyl, 4-hydroxy-butyl, benzyl, chloro-benzyl, bromo-benzyl, methyl-benzyl, methoxy-benzyl or allyl.

U.S. Pat. No. 3,804,849 as well as the Belgian patents disclose that the compounds of the formula I and their non-toxic, pharmacologically acceptable acid addition salts have useful pharmacodynamic properties. More particularly, U.S. Pat. No. 3,804,849 discloses that the compounds possess hypotensive, sedative, antitussive and antiphlogistic properties; the compounds disclosed in Belgian Pat. No. 684,415 are said to have analgesic, sedative, antitussive, antipyretic and antiphlogistic properties; and the compounds disclosed in Belgian Pat. No. 771,330 are said to possess hypotensive, sedative, antitussive and/or antiphlogistic properties.

Moreover, the Belgian patents above referred to state that the thiazolo derivatives of the formula I, where $R_1$ is alkyl of 1 to 4 carbon atoms or allyl, n is 2, and X is sulfur, are particularly effective hypotensives, and that the oxazolo derivatives, where $R_1$ is hydrogen, alkyl of 1 to 4 carbon atoms, hydroxy-(alkyl of 1 to 4 carbon atoms) or allyl, n is 2, and X is oxygen, are particularly effective antitussives.

In addition, in European patent application EP-Al 0,005,732 it is disclosed that compounds of the formula I where n is 2 also exhibit antianginous activity.

For medicinal purposes the sole route of administration disclosed in the prior art is internal, i.e. perorally or parenterally. The average single dose in Belgian Pat. No. 684,415 is disclosed to be 0.5 to 10 mgm for adults; in Belgian Pat. No. 771,330 it is disclosed to be 0.2 to 10 mgm, preferably 0.2 to 5 mgm, for adults; and according to European application EP-Al 0,005,732 it is 2 to 10 mgm, preferably 4 to 7.5 mgm, 1 to 4 times daily.

DESCRIPTION OF THE INVENTION

We have discovered that the thiazolo and oxazolo derivatives of the formula I and their non-toxic, pharmacologically acceptable acid addition salts exhibit a decreasing effect upon the intraocular pressure when they are topically applied to the eye at a dosage of 5 to 600 μgm. This effect of the intraocular pressure is therapeutically essential for the treatment of glaucoma. It is particularly noteworthy that the compounds do not produce an undesirable initial increase of the intraocular pressure which is contrary to the object of the therapy.

For the treatment of glaucoma the compounds of the formula I or their non-toxic, pharmacologically acceptable acid addition salts are incorporated as active ingredients into conventional pharmaceutical compositions suitable for topical application to the eye, that is, composition consisting essentially of an inert carrier and an effective intraocular pressure reducing amount of the active ingredient, such as eye drops, eye ointments, eye gels or also eye-specific pharmaceutical carrier systems of the ocusert, ophthalmic rod, or cellulose- or collagen-sponge type. For example, in the case of 0.01 to 3% eye drops the single dose is 1 to 2 drops in each eye, if necessary several times daily, preferably 2 to 4 times daily; that is, the required volume of drops is 0.05 to 4 ml per day. Thus, the daily dose for topical administration is preferably 5 to 120 μgm, but if needed it can be increased to 1600 μgm.

Particularly preferred antiglaucoma compositions pursuant to the present invention are those wherein the active ingredient is a compound of the formula I where
$R_1$ is hydrogen, alkyl of 1 to 4 carbon atoms or allyl,
n is 2, and
X is oxygen or sulfur,
or a non-toxic, pharmacologically acceptable acid addition salt thereof.

Especially preferred are antiglaucoma compositions wherein the active ingredient is one of the following compounds:

2-Amino-6-ethyl-5,6,7,8-tetrahydro-4H-oxazolo[5,4-d]azepine or a non-toxic, pharmacologically acceptable acid addition salt thereof;
2-Amino-6-allyl-5,6,7,8-tetrahydro-4H-oxazolo[5,4-d]azepine or a non-toxic, pharmacologically acceptable acid addition salt thereof; or
2-Amino-6-allyl-5,6,7,8-tetrahydro-4H-thiazolo[5,4-d]azepine or a non-toxic, pharmacologically acceptable acid addition salt thereof;

at a concentration of 0.01 to 1%, preferably 0.2 to 0.5% by weight, based on the total weight of the composition.

The above-indicated novel utility of the compounds of the formula I and their non-toxic, pharmacologically acceptable acid addition salts was ascertained by the test method described below, and the results of these tests for two species of the genus are shown in the table, where
A=2-Amino-6-ethyl-5,6,7,8-tetrahydro-4H-oxoazolo[4,5-d]azepine dihydrochloride, and
B=2-Amino-6-allyl-5,6,7,8-tetrahydro-4H-thiazolo[4,5-d]azepine dihydrochloride. The tests were performed on white New Zealand rabbits of both sexes having a body weight of 2.5 to 3 kg. Each rabbit was used for 4 tests at intervals of at least 3 days between tests.

The intraocular pressure was measured tonometrically with an Alcon Applanation Pneumotonograph (APTG) calibrated for the human eye. By means of a factor obtained by comparison of the manometric values and APTG values in rabbits anesthetized with urethane, the so-called real pressures were determined. Moreover, before each measurement the cornea was anesthetized with 20 μl of an 0.05% oxybuprocain [2-(diethylamino)-ethyl-4-amino-3-butoxy-benzoate] solution.

The test compound was dropped at different concentrations directly into each eye, 2 drops (50 μl) per eye. The following table shows the results which were obtained.

| Compound A Concentration | Reduction of the intraocular pressure in % after one hour |
| --- | --- |
| 0.3% | −15 |
| 1.0% | −21 |
| 3.0% | −32 |

| Compound B Concentration | Values of the intraocular pressure in mmHg after one hour |
| --- | --- |
| 0.01% | 15 |
| 0.03% | 14.5 |
| 0.3 | 13 |
| 1.0 | 10 |

Furthermore, the compounds of the formula I and their non-toxic, pharmacologically acceptable acid addition salts show good compatibility. For example, compound A has an oral $LD_{50}$ of 2.210 mg/kg in the mouse, and compound B has an oral $LD_{50}$ of 455 mg/kg in the mouse.

The following examples illustrate a few topical antiglaucoma pharmaceutical compositions comprising a compound of the present invention as an active ingredient and represent the best modes contemplated of using the invention.

EXAMPLE 1

Eye Drops

The drop solution is compounded from the following ingredients:

| | |
| --- | --- |
| 2-Amino-6-allyl-5,6,7,8-tetrahydro-4H—thiazolo[5,4-d]azepine dihydrochloride | 50.0 mg |
| Citric acid monohydrate | 29.0 mg |
| Sodium monohydrogen phosphate dihydrate | 140.0 mg |
| Sodium chloride | 13.0 mg |
| Benzalconium chloride | 2.0 mg |
| Water for injection    ad | 10.0 ml |

Preparation:

The main amount of the water for injection is filled into a graduated vessel, and the active ingredient, the buffer substances, the isotonic agent, and the preservative are successively completely dissolved therein while stirring. After filtration through a membrane filter, the solution is filled into brown 10 ml-bottles equipped with a dropping spout.

EXAMPLE 2

Eye Ointment

The ointment is compounded from the following ingredients:

| | |
| --- | --- |
| 2-Amino-6-allyl-5,6,7,8-tetrahydro-4H—thiazolo[5,4-d]azepine dihydrochloride | 25.0 mg |
| Sodium monohydrogen phosphate dihydrate | 10.0 mg |
| Benzalconium chloride | 0.1 mg |
| Sodium chloride | 9.0 mg |
| Water for injection    ad | 1.0 ml |
| Ointment    ad | 10.0 gm |
| Paraffinium liquidum | 30% |
| Vaselinium album | 60% |
| Cetyl alcohol | 3% |
| Wool wax alcohol | 7% |

Preparation:

The pH-correcting agent, the preservative and the isotonic agent are successively added to a solution of the active ingredient in the water for injection. After filtering the resulting solution through a 0.2 μm membrane filter, the filtrate is added to the ointment base which has previously been hot air-sterilized, and the mixture is homogenized. The resulting emulsion is evacuated to remove trapped air while stirring and then filled into ointment tubes.

If the ointment is packaged in disposable single-dose packages, the preservative can be omitted.

EXAMPLE 3

Aqueous Eye Gel

The gel is compounded from the following ingredients:

| | |
| --- | --- |
| 2-Amino-6-allyl-5,6,7,8-tetrahydro-4H—thiazolo[5,4-d]azepine dihydrochloride | 50.0 mg |
| Methyl p-hydroxybenzoate/propyl p-hydroxybenzoate (9:1) | 10.0 mg |
| High molecular weight colloidal carboxyvinyl polymer (CARBOPOL) | 100.0 mg |
| Triethanolamine | 200.0 mg |
| Water for injection    ad | 20.0 gm |

Preparation:

The active ingredient and the preservative are dissolved, while stirring, in the water for injection. The solution is added to a gel which is prepared by adding triethanolamine to a carbopol suspension, and the mixture is homogenzied. Under aseptic conditions the resulting aqueous gel is filled into tubes or into disposable single-dose packages; in the latter case a preservative is not necessary.

EXAMPLE 4

Collagen Fleece/Collagen Film

| | |
| --- | --- |
| 2-Amino-6-allyl-5,6,7,8-tetrahydro-4H—thiazolo[5,4-d]azepine dihydrochloride | 0.05 mg |
| Water for injection (volatile constituent) | 0.01 ml |

Preparation:

The aqueous, sterile-filtered solution of active ingredient is spread under aseptic cond-tions on fleeces of native collagen (thickness approximately 0.3–1 mm), which are prepared in conventional manner and dried under mild conditions. Form the fleeces impregnated with the active ingredient shaped pieces were stamped out containing a therapeutic single dose of 0.05 mg.

The collagen films are prepared in modified manner by adding the solution of the active ingredient a priori to the conventional solution, which is necessary for the preparation of films. After evaporation of the water (film-formation) a foil with a homogeneous surface dose is obtained, from which film pieces with a therapeutic single dose of 0.05 mg are cut out (thickness approximately 0.1 mm, 0.5 cm²).

After placement into the conjunctival sac, the collagen fleece pieces swell up in the lacrimal fluid, and the collagen films dissolve in the lacrimal fluid, thereby making the active ingredient available for penetration through the cornea.

EXAMPLE 5

Ophthalmic Rods

The active ingredient/carrier solution is compounded from the following ingredients:

| | |
|---|---|
| 2-Amino-6-allyl-5,6,7,8-tetrahydro-4H—thiazolo[5,4-d]azepine dihydrochloride | 0.005 mg |
| Hydroxyethyl cellulose | 0.5 mg |
| Water for injection (volatile constituent) | 0.01 ml |

Preparation:

The sterile-filtered or heat-sterilized active ingredient/carrier solution is applied to sterile rods in conventional manner, whereby a therapeutic dose of 5 microgram remains on the rod. After touching the conjunctival sac-mucosa with such a rod this amount of active ingredient spontaneously dissolves in the lacrimal fluid.

Any one of the other compounds embraced by formula I or a non-toxic, pharmacologically acceptable acid addition salt thereof may be substituted for the particular active ingredient in Examples 1 through 5. Likewise, the amount of active ingredient in these illustrative examples may be varied to achieve the dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of treating glaucoma in a warm-blooded animal, which comprises topically administering to the affected eye of said animal an effective intraocular pressure reducing amount of a compound of the formula

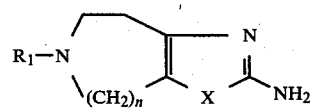

wherein
$R_1$ is hydrogen, alkyl of 1 to 4 carbon atoms, hydroxy-(alkyl of 1 to 4 carbon atoms), benzyl, halobenzyl, methyl-benzyl, methoxy-benzyl or allyl;
X is oxygen or sulfur; and
n is 2;
or a non-toxic, pharmacologically acceptable acid addition salt thereof.

2. The method of claim 1, wherein
$R_1$ is hydrogen, alkyl of 1 to 4 carbon atoms or allyl,
n is 2, and
X is oxygen or sulfur.

3. The method of claim 1, where said compound is 2-amino-6-ethyl-5,6,7,8-tetrahydro-4H-oxazolo[5,4-d]azepine or a non-toxic, pharmacologically acceptable acid addition salt thereof.

4. The method of claim 1, where said compound is 2-amino-6-allyl-5,6,7,8-tetrahydro-4H-oxazolo[5,4-d]azepine or a non-toxic, pharmacologically acceptable acid addition salt thereof.

5. The method of claim 1, wherein said compound is 2-amino-6-allyl-5,6,7,8-tetrahydro-4H-thiazolo[5,4-d]azepine or a non-toxic, pharmacologically acceptable acid addition salt thereof.

6. The method of claim 1, where said intraocular pressure reducing amount is 5 to 600 μgm.

7. The method of claim 1, where said intraocular pressure reducing amount is 20 to 500 μgm.

* * * * *